United States Patent [19]

Picard

[11] Patent Number: 4,898,713
[45] Date of Patent: Feb. 6, 1990

[54] PROCESS FOR STERILIZING A TIGHT ENCLOSURE AND INSTALLATION FOR PERFORMING THIS PROCESS

[75] Inventor: Claude Picard, Nanterre, France

[73] Assignee: Societe Nouvelle d'Exploitation La Calhene, Velizy-Villa coublay, France

[21] Appl. No.: 166,366

[22] Filed: Mar. 10, 1988

[30] Foreign Application Priority Data

Mar. 30, 1987 [FR] France ................................ 87 04393

[51] Int. Cl.$^4$ ............................ A61L 2/20; A61L 2/24
[52] U.S. Cl. .......................................... 422/3; 422/28; 422/32; 422/33; 422/298; 422/299; 422/305; 422/62; 422/114
[58] Field of Search .................... 422/3, 28, 29, 32–37, 422/298, 299, 305, 62, 114

[56] References Cited

U.S. PATENT DOCUMENTS

| | | | |
|---|---|---|---|
| 3,549,312 | 12/1970 | Ernst | 422/3 |
| 3,598,516 | 8/1971 | Shull et al. | 422/34 |
| 3,598,517 | 8/1971 | Beecher | 422/34 |
| 4,374,087 | 2/1983 | Hallström | 422/34 |
| 4,410,492 | 10/1983 | Kaye | 422/34 |
| 4,764,351 | 8/1988 | Hennebert et al. | 422/33 |

FOREIGN PATENT DOCUMENTS

| | | |
|---|---|---|
| 3523310 | 2/1987 | Fed. Rep. of Germany . |
| 2335240 | 7/1977 | France . |
| 2352551 | 12/1977 | France . |
| 2354779 | 1/1978 | France . |
| 2508316 | 12/1982 | France . |

*Primary Examiner*—Barry S. Richman
*Assistant Examiner*—Timothy M. McMahon
*Attorney, Agent, or Firm*—Dennis P. Clarke

[57] ABSTRACT

For sterilizing a tight enclosure (10) equipped with a ventilation and filtration circuit (14), said enclosure is isolated and the internal relative humidity level is lowered by means of an assembly (50) incorporating a drying cartridge (54). The sterilizing agent (46) is then introduced through a closed circuit (30) until a relative humidity level close to the dew point is obtained. The sterilizing agent is kept in the enclosure for a given contact time, before scavenging said agent by means of the ventilation and filtration circuit (14).

7 Claims, 1 Drawing Sheet

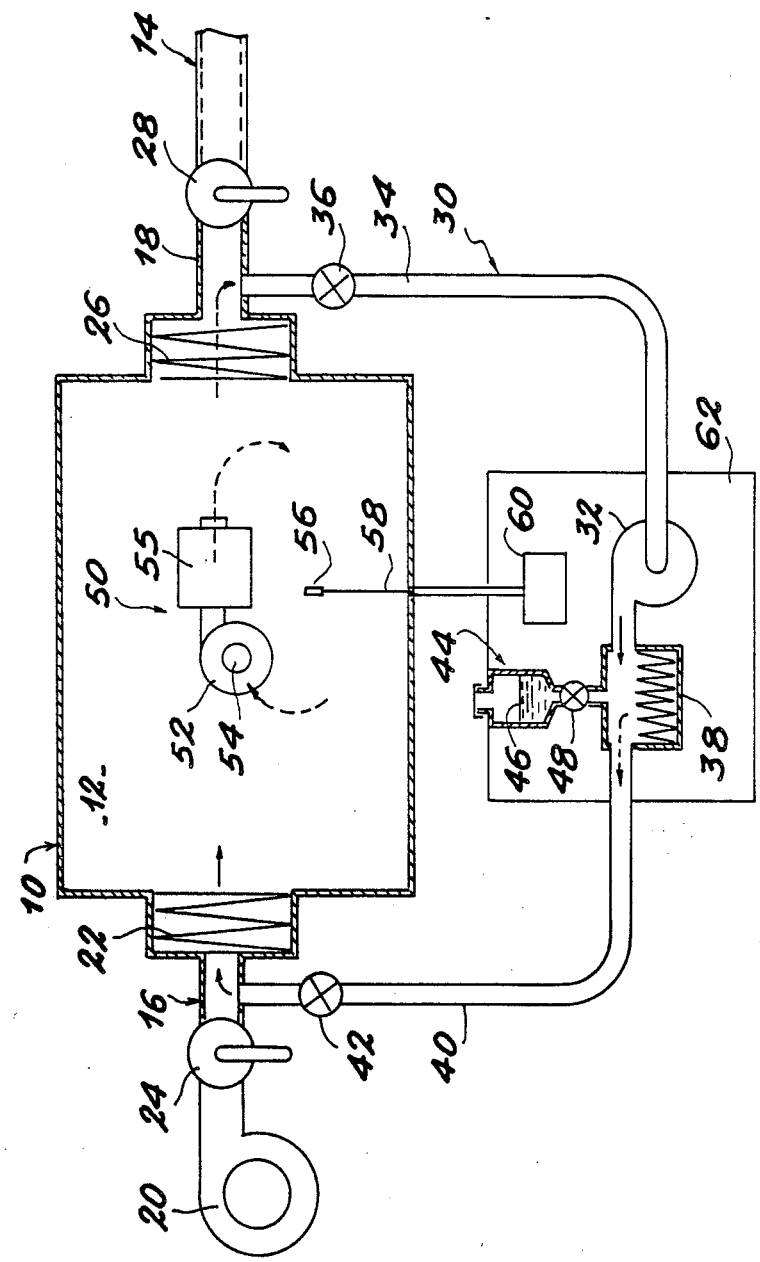

PROCESS FOR STERILIZING A TIGHT ENCLOSURE AND INSTALLATION FOR PERFORMING THIS PROCESS

DESCRIPTION

The invention relates to a process for sterilizing a tight enclosure equipped with a ventilation and filtration circuit, as well as to installation for performing this process.

Patent No. FR-A-2 475 679 describes a tight enclosure equipped with a ventilation and filtration circuit, which more particularly has a supply pipe and a discharge pipe issuing into said enclosure, filters being placed in the pipes in the vicinity of their ends issuing into the enclosure. The latter can be sterilized by means of a sterilizer connected to the supply pipe upstream of the filters. When it is wished to sterilize the enclosure, the sterilizing chemical agent supplied by said sterilizer is introduced into the enclosure by operating the ventilation and filtration circuit. Such an installation has the advantage of passing the sterilizing agent through filters, which guarantees a perfect sterilization of the entire internal volume of the enclosure.

However, the sterilization obtained with the aid of the installation described in the above document is performed by using a ventilation and filtration circuit, i.e. dynamically and by an open circuit. Thus, the sterilization time is relatively long and a large quantity of sterilizing agent is necessary.

Moreover, there is no control of the relative humidity or hygrometry within the enclosure, so that there is a significant risk of exceeding the saturation or dew point within the enclosure. Such an exceeding of the dew point is particularly unfavourable, because it leads to large-scale corrosion of the enclosure walls and of all the equipment contained therein, togehter with a risk of deterioration of the filter by tearing as a result of wetting.

It is also known to sterilize a tight enclosure by introducing a sterilizer or atomizer into the same. Sterilization is then performed after closing the supply and discharge pipes of the ventilation and filtration circuit. Compared with the aforementioned procedure, this procedure has the advantage of ensuring a faster sterilization, because the sterilization takes place in a closed circuit and in a static manner.

However, this procedure suffers from two disadvantages. Firstly the sterilizing agent does not pass through the filters, so that it is not possible to be sure that the entire volume is sterile. In addition, there is no hygrometry control, so that the aforementioned risks again occur. In the case where an atomizer is used, the corrosive effects on the walls and on the equipment, together with the deterioration of the filters are virtually inevitable, because a sterilizing mist with 100% relative humidity is vaporized.

The invention is directed at a process for sterilizing a tight enclosure, according to which the sterilizing agent is circulated through the filters of the ventilation and filtration circuit in order to improve the sterilization quality. The sterilizing agent is introduced by a closed circuit permitting a static sterilization, which reduces the time necessary for the sterilization process and the humidity is checked, so as not to exceed the saturation or dew point within the enclosure.

According to the invention, this result is obtained by means of a process for the sterilization of a tight enclosure defining a closed volume and equipped with a ventilation and filtration circuit having a supply pipe and a discharge pipe issuing into the enclosure and provided with filtration means, characterized in that it comprises the following successive stages:
  closing the ventilation and filtration circuit upstream of the filtration means of the supply pipe and downstream of the filtration means of the discharge pipe.
  drying the closed volume defined by the enclosure until a given lower relative humidity is obtained.
  introduction of a sterilizing agent into said volume until a given higher relative humidity is obtained and for which the volume is saturated with sterilizing agent, by using a closed circuit connected to the supply pipe upstream of the filtration means and to the discharge pipe downstream of the filtration means.
  sterilization by maintaining the sterilizing agent in the closed volume for a given contact time and
  scavenging the closed volume by opening and using the ventilation and filtration circuit.

In a preferred embodiment of the invention, the closed volume is dried by circulating the atmosphere within said volume through drying means.

Preferably, in order to permanently ensure an ambient distribution, the atmosphere within the enclosure is stirred up by also circulating said atmosphere during the sterilizing agent introduction, sterilization and scavenging periods.

The drying of the atmosphere within the enclosure is preferably carried out until a relative humidity below approximately 30% is obtained, which makes it possible to significantly increase the sterilizing agent introduction range ensuring a better saturation of said agent. So as not to exceed the dew point within the enclosure, the sterilizing agent introduction is stopped on reaching a relative humidity exceeding roughly 85%.

Although other sterilizing agents such as formaldehyde can be used, preference is given to the use of p-acetic acid with which the contact time is below 1 hour.

The invention also relates to an installation for performing the sterilization process defined hereinbefore and which is characterized in that it comprises:
  a drying and stirring assembly which can be placed within the enclosure, said assembly incorporating a fan, drying means and filtration means connected in series.
  a sterilizing agent introduction circuit, which can be connected to said parts of the pipes, respectively upstream of the filtration means of the supply pipe and downstream of the filtration means of the discharge pipe, said circuit having in series a blower and an evaporator supplied with sterilizing agent via a valve, as well as inlet and outlet valves making it possible to isolate the circuit from the closed volume during sterilization and
  a relative humidity measuring probe, which can be placed with the enclosure and associated with a control member for the aforementioned valves in order to automatically close the latter when the relative humidity reaches said upper relative humidity level.

BRIEF DESCRIPTION OF THE DRAWING

A preferred embodiment of the invention will now be described in non-limitative manner with reference to the drawing, which diagrammatically shows an installation for sterilizing a tight enclosure making it possible to perform the process of the invention.

The drawing diagrammatically shows a tight enclosure 10 defining a closed volume 12. The enclosure 10 can be used in medicine, pharmaceutics, biology or electronics. The enclosure dimensions vary as a function of its use and for information purposes the volume can vary between 2 and 20 m$^3$.

In conventional manner, enclosure 10 is equipped with a ventilation and filtration circuit 14 having a supply pipe 16 and a discharge pipe 18. Supply pipe 16 is equipped with a fan 20, which sucks up the air outside in order to force it back into the closed volume 12 through one or more filters 22 mounted in that part of pipe 16 issuing into the enclosure 10. A valve 24 is placed in supply pipe 16 upstream of filter 22.

The discharge pipe 18 enables the filtered air allowed to enter the interior of volume 12 through pipe 16 to be discharged to the outside, in order to ensure a replenishment of the atmosphere prevailing within volume 12. The discharge pipe 18 is also equipped with one or more filters 26 in its part adjacent to enclosure 32. A valve 28 is also placed in pipe 18 downstream of filter 26.

Under normal working conditions within enclosure 10, valves 24 and 28 are open and fan 20 is operated. A ventilation of the atmosphere within the enclosure 10 is consequently ensured through filters 22 and 26.

According to the invention, when the working volume 12 within enclosure 10 has to be sterilized prior to use, with said enclosure and its ventilation and filtration circuit 14 is associated a sterilization installation, whose various components will now be described.

This installation firstly comprises a closed circuit 30 used for introducing a sterilizing agent into the enclosure, following the closing of valves 24 and 28. This closed circuit 30 comprises a blower 32, whose suction opening is connected to one end of a suction pipe 34, the opposite end of the latter being connectable to the discharge pipe 18 of the ventilation and filtration circuit 14 between filter 25 and valve 28. In the vicinity of pipe 18, pipe 34 is equipped with an electrovalve 36.

Circuit 30 also comprises a constant level evaporator 38, whereof an intake tube communicates with the delivery opening of the blower 32. The discharge tube of the evaporator 38 is connected to a first end of a delivery pipe 40. The opposite end of pipe 40 can be connected to the supply pipe 16 of the ventilation and filtration circuit between valve 24 and filter 22. Pipe 40 is also equipped with an electrovalve 42 close to pipe 16.

As is diagrammatically illustrated by the drawing, a tank 44 containing the chemical sterilizing agent 46 is placed above evaporator 38, so as to supply sterilizing agent 46 to the latter by gravity. An electrovalve 48 is interposed between tank 44 and evaporator 38 to ensure the control and interruption of the supply to the latter.

Apart from the closed circuit 30 making it possible to introduce the sterilizing agent into enclosure 10 and the adjoining parts of pipes 16, 18 having filters 22 and 26, the inventive sterilization installation comprises an assembly for drying and stirring up the atmosphere within the closed volume 12 and designated by reference 50 in the drawing.

Assembly 50, which is placed directly within the closed volume 12, comprises a fan 52 which directly sucks the air within the volume 12. The air sucked by fan 52 is forced back into the interior of the closed volume 12 through a drying cartridge 54 and then a filter 55. As will be shown in greater detail hereinafter, assembly 50 has the double function of ensuring the drying of volume 12 before putting circuit 30 into operation and permits a permanent stirring up of the air contained in said volume along the different sterilization stages.

Finally, the sterilization installation according to the invention comprises a probe 56 located within enclosure 10 and used for permanently measuring the relative humidity or hygrometry within said enclosure. Probe 56 is connected by an electric conductor 58 to an electronic circuit 60 located outside the enclosure and used for automatically controlling the closure of electrovalves 36, 42 and 48 when the relative humidity within the enclosure reaches a given maximum threshold.

In practice and as is diagrammatically shown in the drawing, electronic circuit 60, pump 32, evaporator 38, tank 44 and valve 48 are mounted within a single box or casing in order to form an apparatus 62.

According to the invention, when it is wished to sterilize an enclosure 10 with the aid of the aforementioned apparatus, pipes 34 and 40 are respectively connected to the discharge pipe 18 and supply pipe 16 of the ventilation and filtration circuit 14 of the enclosure. For this purpose, these supply and discharge pipes are equipped with bypasses or taps, which are normally closed by not shown plugs or stoppers.

Valves 24 and 28 of circuit 14 are then closed, in order to isolate a closed volume including the volume 12 within enclosure 10 and those parts of the ends of pipes 16 and 18 adjoining said enclosure and in which are fitted the filters 22 and 26. Moreover, the hygrometric probe 56 and the assembly 50 are placed within said tight enclosure 10. Tank 44 is then filled with a sterilizing agent 46 and a new element is introduced into the constant level evaporator 38.

When these preparations are completed, the inventive process is performed in the form of a first stage consisting of drying the volume 12 within the tight enclosure 10. To this end, with valves 36 and 42 closed, fan 52 is put into operation in order to circulate the air contained in volume 12 over the drying cartridge 54 and through filter 55. This drying phase is continued until the relative humidity measured by probe 56 within the volume 12 reaches a lower value, which is generally close to 30%. The electronic circuit 60 associated with the probe indicates to the operator when this value is reached, e.g. by displaying an appropriate signal.

It should be noted that the duration of this first stage is essentially dependent on the relative humidity initially prevailing within the enclosure and the volume within the same. However, this time still remains relatively short in view of the fact that the air confined within the enclosure circulates in closed circuit manner on the drying cartridge 54.

When this first stage is ended, circuit 30 is put into operation in order to introduce the sterilizing agent 46 contained in tank 44 into the volume 12 located within the enclosure 10. This sterilizing agent is preferably p-acetic acid, but can also be constituted by any other chemical sterilizing agent, such as formaldehyde.

In order to carry out this introduction, valves 36 and 42 are open, as is the valve 48, which supplies the evaporator 38 with sterilizing agent 46, whilst maintaining constant the level of said sterilizing agent with said evaporator. Simultaneously, blower 32 is put into operation, which has the effect of circulating the air contained in the volume 12 within enclosure 10 into evaporator 38 via circuit 30. In view of the fact this this air has been previously dried with the aid of assembly 50, in a relatively short time a large amount of sterilizing agent vapour is introduced into the enclosure.

It should be noted that the air flow rate within the circuit 30 produced by blower 32 is relatively high, so that it produces, particularly in filters 22, 26, a certain pressure tending to evaporate the liquid sterilizing agent droplets, which tend to be fixed to these filters. Moreover, the sections of pipes 34 and 40 are smaller than those of pipes 16 and 18, in order that this effect can be obtained no matter what the dimensions of enclosure 10 to be sterilized.

During the opereation of circuit 30 making it possible to introduce the sterilizing agent into the volume 12 defined by enclosure 10, fan 52 continues to operate in order to permanently homogenize the air contained within the enclosure. Thus, the sterilizing agent concentration is substantially uniform at all times and at all points of the enclosure.

When the probe 56 detects within enclosure 10 a relative humidity level corresponding to the saturation of the air with sterilizing agent, electronic circuit 60 automatically controls the stoppage of blower 32 and the closing of valves 36, 42 and 48. In practice, this saturation is reached when the relative humidity within enclosure 10 is close to 85% ($\pm$5%). By in this way limiting the introduction of the sterilizing agent to a value corresponding to the dew point within volume 12, it is possible to avoid the disadvantages linked with exceeding said dew point, such as the corrosion of the enclosure and equipment contained therein and the risk of the filters tearing. Moreover, in view of the fact that the sterilizing agent is introduced in closed circuit form, the time necessary for reaching saturation is relatively short.

The inventive process then continues with a stage corresponding to the actual sterilization and during which the sterilizing agent trapped within volume 12 is kept in contact with the atmosphere within the enclosure for a time which is a function of the nature of the sterilizing agent used. Thus, in the case where the sterilizing agent is p-acetic acid, the duration of said contact phase is less than 1 hour (e.g. approximately 40 minutes), whereas said contact phase reaches approximately 12 hours when the sterilizing agent used is formaldehyde.

During this contact phase ensuring the actual sterilization, fan 52 continues to operate, with a view to homogenizing the air contained in volume 12. At the end of this contact phase, the sterilizing agent is discharged by scavenging volume 12. This scavenging is carried out by opening valves 24, 28 of the ventilation and filtration circuit 14 and then by operating fan 20. Simultaneously, fan 52 of assembly 50 continues to operate.

In order to rinse the sterilization circuit 30, blower 32 can again be put into operation for approximately 15 minutes following the opening of valves 36 and 42, the sterilizing agent supply valve 48 being kept closed. This operation can be performed either during the previously described scavenging phase, or optionally following said operation.

When the volume 12 within enclosure 10 has been scavenged, as well as following the rinsing of circuit 30, pipes 34 and 40 can be disconnected from pipes 18 and 16. Assembly 50 and probe 56 can also be removed from enclosure 10. The latter can then be used for carrying out the desired operations therein in a sterile atmosphere.

The introduction and extraction of assembly 50 and probe 56 into and out of enclosure 10 are performed by means of known tight transfer devices, which do not form part of the present invention.

I claim:

1. Process for the sterilization of a tight enclosure having a closed volume and equipped with a ventilation and filtration circuit, which circuit has a supply pipe with a supply filter and a discharge pipe with a discharge filter, the supply pipe and the discharge pipe each connected to the tight enclosure defining the closed volume, the steps of the process comprising in order:
   (a) closing the ventilation and filtration circuit upstream of the supply filter and downstream of the discharge filter;
   (b) while the ventilation and filtration circuit remains closed:
      I. drying the closed volume defined by the tight enclosure until a given lower relative humidity is obtained;
      II. introducing a sterilizing agent into the closed volume until a given higher relative humidity is obtained, the sterilizing agent being introduced by using a closed circuit connected to the supply pipe upstream of the supply filter and to the discharge pipe downstream of the discharge filter;
      III. sterilizing the closed volume by maintaining the sterilizing agent in the closed volume for given contact time; and
   (c) scavenging the closed volume by opening and using the ventilation and filtration circuit, and wherein the drying of the closed volume is accomplished by circulating the atmosphere within said volume through a drying means which is located within the closed volume.

2. Process according to claim 1 wherein the lower relative humidity level is close to 30%.

3. Process according to claim 1 wherein the upper relative humidity level is close to 85%.

4. Process according to claim 1 wherein p-acetic acid is used as the sterilizing agent, the contact time being less than 1 hour.

5. Process of claim 1 wherein said given higher relative humidity corresponds to the saturation of the volume with sterilizing agent.

6. A system for performing a sterilization process comprising a tight enclosure defining a closed volume and equipped with a ventilation and filtration circuit, which circuit includes a supply pipe having a supply filter and a discharge pipe having a discharge filter, said system further comprising:
   a drying and stirring assembly within the enclosure, said assembly incorporating a fan, drying means, and filtration means connected in series; a sterilizing agent introduction circuit connected to the supply pipe upstream of the supply filter and connected to the discharge pipe downstream from the discharge filter, said circuit having in series a blower and an evaporator supplied with sterilizing agent via a sterilizing agent valve, said circuit further having inlet and outlet valves for isolating the circuit from the closed volume during sterilization; and a relative humidity measuring probe within the closed volume and connected to a control means which automatically stops the introduction of sterilizing agent into the enclosed volume upon the relative humidity within the enclosed volume reaching a given upper relative humidity level.

7. The system of claim 6 wherein said control means automatically turns off said blower and automatically closes said sterilizing agent valve, inlet valve, and outlet valve upon the relative humidity within the enclosed volume reaching said given upper relative humidity level.

* * * * *